United States Patent
Dalmases Barjoan et al.

(10) Patent No.: US 8,304,426 B2
(45) Date of Patent: Nov. 6, 2012

(54) POLYMORPHIC FORM OF GRANISETRON BASE, METHODS FOR OBTAINING IT AND FORMULATION CONTAINING IT

(75) Inventors: Pere Dalmases Barjoan, Sant Feliu de Llobregat (ES); Reyes Herbera Espinal, Agramunt (ES); Angel Maria Alvarez Larena, Castellbisbal (ES)

(73) Assignee: Inke, S.A., Castellbisbal (ES)

( * ) Notice: Subject to any disclaimer, the term of this patent is extended or adjusted under 35 U.S.C. 154(b) by 463 days.

(21) Appl. No.: 12/664,153

(22) PCT Filed: Dec. 20, 2007

(86) PCT No.: PCT/EP2007/064319
§ 371 (c)(1), (2), (4) Date: Mar. 10, 2010

(87) PCT Pub. No.: WO2008/151677
PCT Pub. Date: Dec. 18, 2008

(65) Prior Publication Data
US 2010/0204264 A1    Aug. 12, 2010

Related U.S. Application Data

(60) Provisional application No. 60/946,163, filed on Jun. 26, 2007.

(30) Foreign Application Priority Data

Jun. 13, 2007  (ES) .................................. 200701630

(51) Int. Cl.
*A61K 31/439*  (2006.01)
*C07D 451/14*  (2006.01)
*A61P 1/08*  (2006.01)

(52) U.S. Cl. ........................................ 514/299; 546/112
(58) Field of Classification Search .................. 546/112; 514/299
See application file for complete search history.

(56) References Cited

FOREIGN PATENT DOCUMENTS

| EP | 0200444 A | 11/1996 |
|---|---|---|
| ES | 2129349 | 6/1999 |
| WO | WO97/30049 | 8/1997 |

OTHER PUBLICATIONS

International Search Report for PCT/EP2007/064319, completed Mar. 25, 2008.

*Primary Examiner* — D M Seaman
*Assistant Examiner* — Niloofar Rahmani
(74) *Attorney, Agent, or Firm* — Barnes Thornburg LLP

(57) ABSTRACT

Relates to a new polymorphic form of Granisetron base, Form I, to methods for obtaining thereof, to the method for obtaining Granisetron.HCl and its use for preparing pharmaceutical formulations. The Form I is characterized by the X-ray powder diffractogram shown in FIG. 1. Included in summarised form are the methods and solvents for obtaining the Form I: 1) Evaporation of hexane at atmospheric pressure; 2) Evaporation of acetone at atmospheric pressure; 3) Evaporation of toluene at atmospheric pressure; 4) Cooling of a saturated solution of diethyl ether to reflux temperature; 5) Evaporation of 2-propanol atmospheric pressure; 6) Evaporation of tetrahydrofuran at atmospheric pressure; and 7) Cooling of a saturated solution of acetonitrile to reflux temperature.

24 Claims, 6 Drawing Sheets

POLYMORPHIC FORM OF GRANISETRON BASE, METHODS FOR OBTAINING IT AND FORMULATION CONTAINING IT

CROSS REFERENCE TO RELATED APPLICATIONS

This application is the U.S. national phase of PCT/EP2007/064319 filed Dec. 20, 2007. PCT/EP 2007/064319 claims benefit under the Paris Convention to ES P-200701630 filed Jun. 13, 2007 and U.S. Provisional Application Ser. No. 60/946,163 filed Jun. 26, 2007. The disclosures of ES P-200701630, U.S. Provisional Application Ser. No. 60/946, 163, and PCT/EP2007/064319 are hereby incorporated herein by reference.

FIELD OF THE INVENTION

The present invention relates to a new polymorphic form of Granisetron base that shall hereinafter be denominated Form I, to methods for obtaining it, to the method for obtaining Granisetron.HCl from Granisetron base Form I and to the utilisation of this Granisetron base Form I for preparing pharmaceutical formulations.

BACKGROUND OF THE INVENTION

Granisetron base or endo-1-methyl-N-(9-methyl-9-azabicycle[3.3.1]non-3-yl)-1H-indazole-3-carboxamide has the following structure:

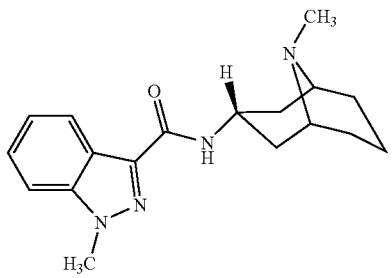

Granisetron acts as an antagonist of 5-HT (5-hydroxytriptamine), is useful as an antiemetic and is marketed in the form of a hydrochloride.

Granisetron was described for the first time in European patent EP 200444 where, in example 6, Granisetron base is described as an oil.

Said European patent describes how to obtain it by reaction between 1-methylindazole-3-carboxylic acid chloride and endo-3-amino-9-methyl-9-azabicycle-[3.3.1]-nonane.

Other processes for preparing it were also disclosed in patent ES2129349, in which the basic form of Granisetron is not isolated, while example 2 of international patent application WO97/30049 again describes it as an oil.

Chemical products in oil form are awkward to use and difficult to purify, since column chromatography is usually required. Moreover, pharmaceutical products in the form of oil are not suitable for pharmaceutical formulations.

Metastable polymorph forms are neither suitable since may change in an uncontrolled way.

A stable polymorph form of said compound have not yet been described and, therefore, nor their crystalline structure.

In order to overcome the disadvantages of the state of the art, the present authors have found a solid form of Granisetron base and a stable polymorphic form thereof.

SUMMARISED DESCRIPTION OF THE INVENTION

A first object of the present invention is to provide a polymorphic form of Granisetron base, also denominated Granisetron base Form I in the present invention.

A second object of the invention is to provide various methods for obtaining said polymorphic Form I.

A third object of the present invention is to provide a pharmaceutical formulation that contains said Granisetron base Form I, together with pharmaceutically acceptable excipients and/or vehicles.

A fourth object of the present invention is to provide the hydrochloride of Granisetron from said Granisetron base Form I.

DEFINITIONS

In the present invention the term "Granisetron base" is taken to mean Granisetron in its basic form, i.e. not forming part of a salt. Said "Granisetron base" is in the form of an oil or is the reaction crude to prepare Granisetron base.

In the present invention the term "Granisetron base solution" is taken to mean Granisetron base dissolved in a suitable solvent or the dissolution of a Granisetron salt in a suitable solvent, followed by basification thereof with a base or a basic solution.

In the present invention the term "water-miscible organic solvent" is taken to mean any organic solvent that can be mixed with water in any proportion that gives rise to a single phase of the two components. Preferable cases are shown in the detailed-description section of the invention.

In the present invention the term "organic solvent partially miscible in water" is taken to mean any organic solvent that can be mixed with water to give a single phase within a range of proportions, but not in all the proportions. Preferable cases are shown in the detailed-description section of the invention.

FIGURES

Here follows in summarised form the method and solvent used: 1) Evaporation of hexane at atmospheric pressure; 2) Evaporation of acetone at atmospheric pressure; 3) Evaporation of toluene at atmospheric pressure; 4) Cooling of a saturated solution of diethyl ether to reflux temperature (according to Example 7); 5) Evaporation of 2-propanol at atmospheric pressure; 6) Evaporation of tetrahydrofuran at atmospheric pressure (according to Example 1); and 7) Cooling of a solution of saturated acetonitrile to reflux temperature.

Figure 6:
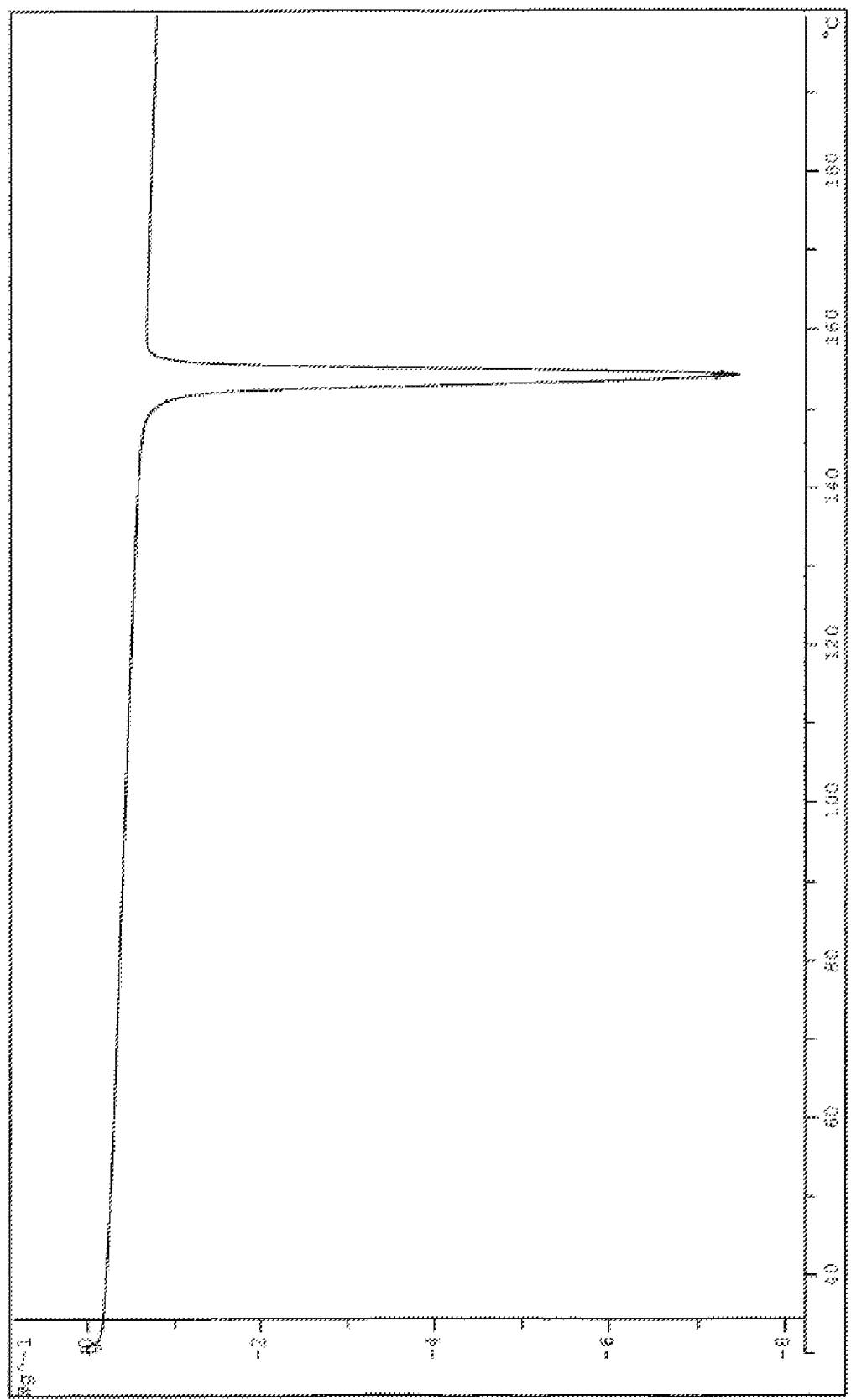

FIG. 6 shows a DSC diagram of Granisetron base Form I according to the invention.

DETAILED DESCRIPTION OF THE INVENTION

Figure 1:
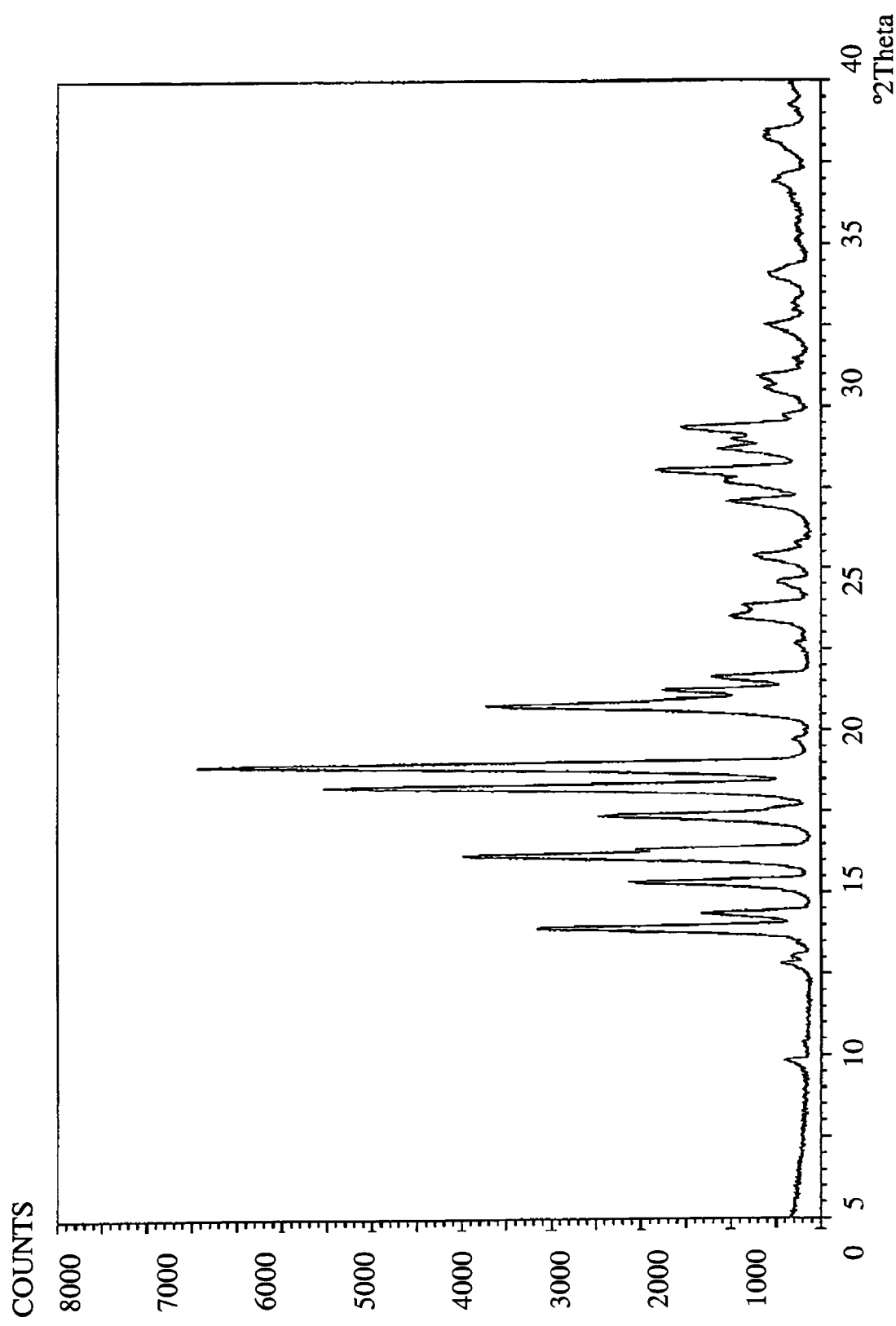
FIG. 1 shows an X-ray powder diffractogram of the Granisetron base Form I.

In accordance with the first object of the invention a polymorphic form of Granisetron base (Form I) is provided that is characterised by having peaks in the X-ray powder diffractogram, in ° of 2θ: 9.8°, 15.4°, 16.2°, 17.4°, 18.3°, 19.0°, 20.8°, 21.2°, 21.7°, 23.5°, 25.4°, 27.1°, 27.7°, 28.1°, 28.7°, 29.0° and 29.3°. FIG. 1 shows a typical example of said diffractogram.

A PHILIPS X' Pert diffractometer provided with a Cu tube and a secondary monochromator made of graphite (wavelength Kα Cu, 1.5419 Å) was used to record the X-ray powder diffractograms. Reception slot: 0.1 mm; Soller: 0.04 rad; antidiffusion slot and divergence slot: 1°.

The relative intensity of the peaks in the various diffractograms of Granisetron base Form I obtained with different solvents or crystallisation techniques varies owing to the different particle sizes and crystalline habits.

Figure 2:
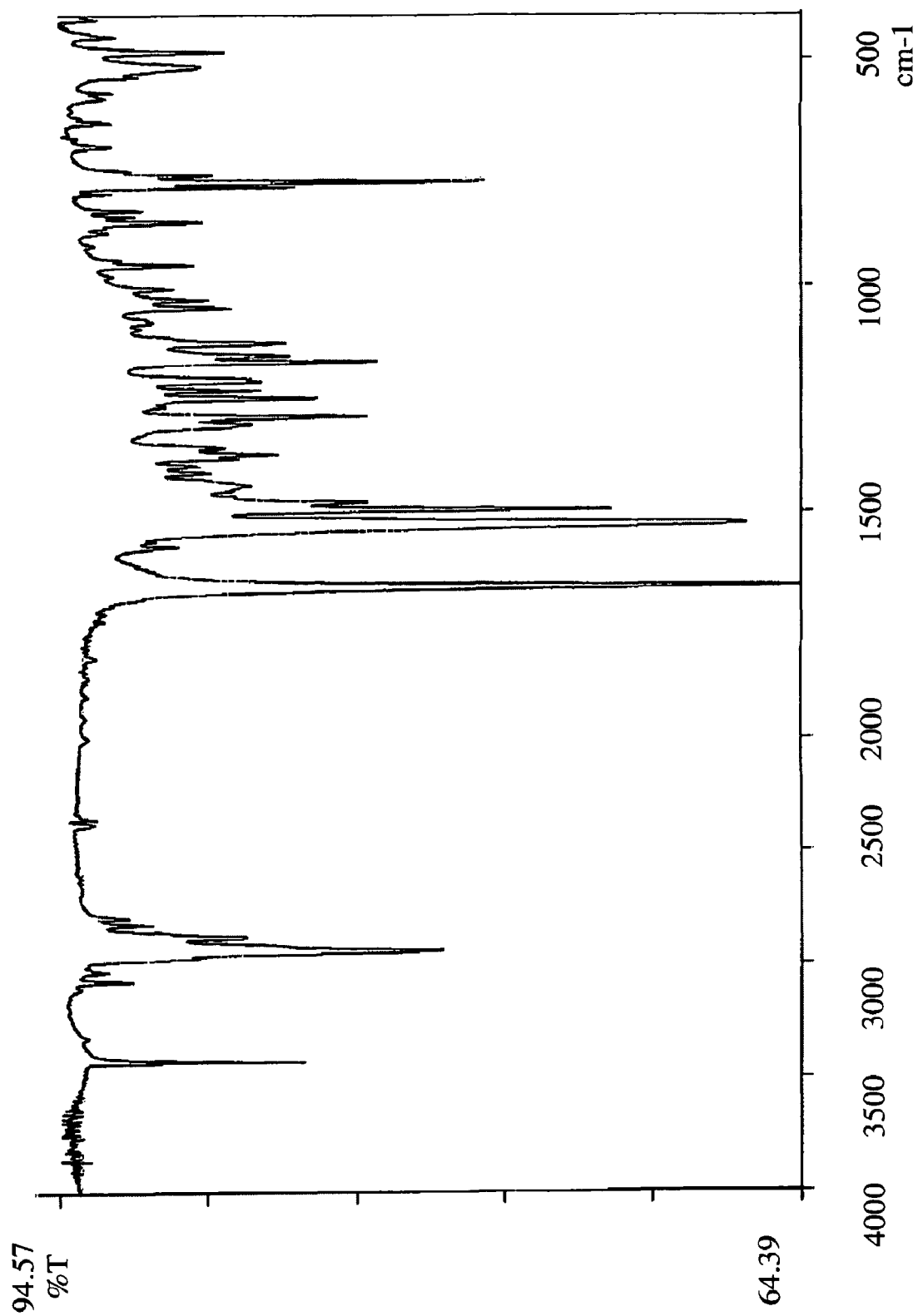
FIG. 2 shows an infrared spectrum of the Granisetron base Form I.

The Granisetron base Form I is also characterised by an infrared (IR) spectrum with the following peaks, in $cm^{-1}$ units: 3420, 2920, 2860, 1670, 1530, 1495, 1285, 1210, 770 and 470. FIG. 2 shows said spectrum.

On the basis of a monocrystal of Granisetron base Form I, obtained by evaporating toluene at atmospheric pressure, it was possible to make a structural study using X-rays. In order to carry out the structural study by X-ray diffraction of monocrystal, a suitable monocrystal was mounted exposed to air on fibreglass, in an Enraf Nonius CAD4 automatic diffractometer. It was irradiated with Kα radiation of the Mo (λ=0.71069 Å) obtained with a graphite monochromator.

Figure 3:
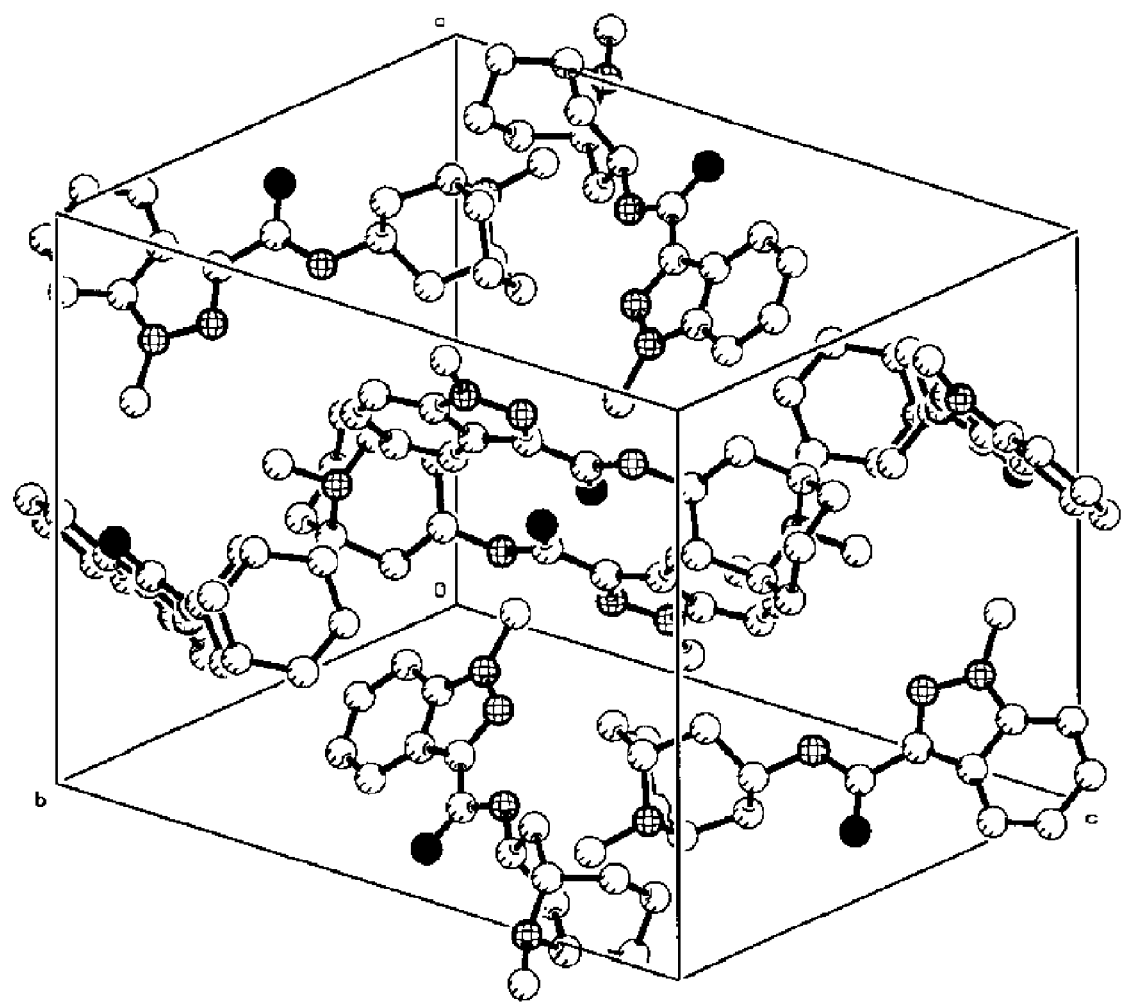
FIG. 3 shows the crystalline structure of Granisetron base Form I.
Figure 4:
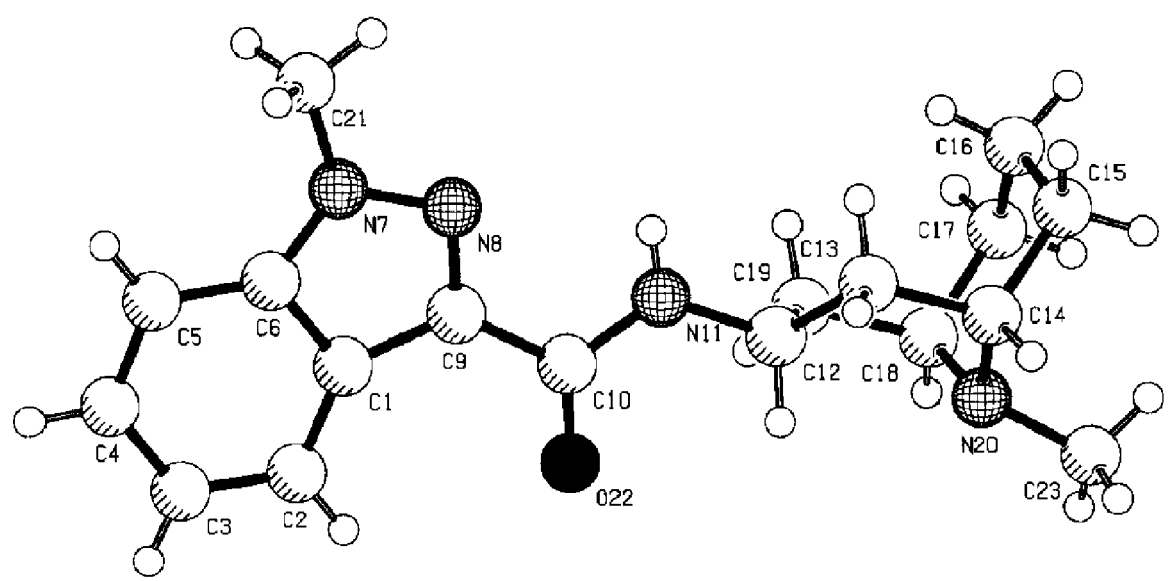
FIG. 4 shows the molecular structure presented by Granisetron base Form I.

It was found that the Granisetron base Form I presents a rhomboid cell with the parameters: a=13.571 (5) Å; b=13.787 (2) Å; c=17.970 (4) Å; α=β=γ=90°. See FIG. 3 for crystalline structure and FIG. 4 for molecular structure.

Table 1 below shows the atomic coordinates ($\times 10^4$ Å) of the asymmetric unit (atoms different from hydrogen) of the crystalline structure of Granisetron base Form I.

TABLE 1

|  | X | Y | Z |
| --- | --- | --- | --- |
| C(1) | 3320(1) | 3177(1) | 5335(1) |
| C(2) | 3949(1) | 3535(2) | 5891(1) |
| C(3) | 3861(2) | 3174(2) | 6593(1) |
| C(4) | 3161(2) | 2462(2) | 6762(1) |
| C(5) | 2533(2) | 2099(2) | 6237(1) |
| C(6) | 2627(1) | 2455(1) | 5512(1) |
| C(7) | 2123(1) | 2257(1) | 4877(1) |
| C(8) | 2433(1) | 2802(1) | 4298(1) |
| C(9) | 3155(1) | 3357(1) | 4566(1) |
| C(10) | 3671(1) | 4058(1) | 4082(1) |
| C(11) | 3387(1) | 4095(1) | 3372(1) |
| C(12) | 3832(1) | 4751(1) | 2834(1) |
| C(13) | 3085(1) | 5061(2) | 2260(1) |
| C(14) | 3559(1) | 5692(2) | 1645(1) |
| C(15) | 3457(2) | 5240(2) | 878(1) |
| C(16) | 4045(2) | 4321(2) | 815(1) |
| C(17) | 5095(2) | 4470(2) | 1065(1) |
| C(18) | 5136(1) | 4961(2) | 1831(1) |
| C(19) | 4729(1) | 4299(2) | 2459(1) |
| C(20) | 4587(1) | 5877(1) | 1853(1) |
| C(21) | 1273(2) | 1620(2) | 4782(1) |
| C(22) | 4325(1) | 4571(1) | 4335(1) |
| C(23) | 5040(2) | 6648(2) | 1419(1) |

Another object of the present invention is to provide different methods for obtaining the Granisetron base Form I.

A first method for obtaining the Granisetron base Form I is characterised in that the following stages are carried out:

i) dissolving the Granisetron base in a suitable polar or apolar organic solvent, in a mixture of such solvents or in a mixture of water-miscible organic solvent and water at room temperature, and ii) then evaporating the solvent or the mixture of solvents to give the Granisetron base Form I.

The solvent can be evaporated at atmospheric pressure or at reduced pressure.

A suitable polar or apolar organic solvent can be selected from methanol, ethanol, 2-propanol, acetone, methyl ethyl ketone, ethyl acetate, acetonitrile, diethyl ether, isopropyl ether, tetrahydrofuran, dioxane, methylene chloride, chloroform, carbon tetrachloride, toluene or hexane.

The water-miscible organic solvent can be selected from methanol, ethanol, 2-propanol or acetone.

A second method for obtaining the Granisetron base Form I is characterised in that the following stages are carried out:

i) dissolving the Granisetron base in a suitable polar or apolar organic solvent or in a mixture of water-miscible organic solvent and water at a temperature between 30° C. and the reflux temperature of the selected solvent, ii) then, cooling the solution to a temperature between 0° C. and room temperature to induce crystallisation of a solid, and iii) filtering said solid to obtain Granisetron base Form I.

The solvents used in this second alternative method are the same as those listed in the first method above.

A third method for obtaining the Granisetron base Form I is characterised in that the following stages are carried out:

i) dissolving Granisetron base in a water-miscible organic solvent or partially water-miscible organic solvent, and ii) then, pouring said solution onto water to precipitate the Granisetron base Form I.

Thus, Granisetron base Form I is obtained by filtering the resulting suspension.

The partially water-miscible organic solvent is acetonitrile. The other solvents are those listed above.

A fourth alternative method for obtaining the Granisetron base Form I is characterised in that the following stages are carried out:

i) dissolving the Granisetron base in a liquid carboxylic acid or in an acidic solution of carboxylic acid or mineral acid, and ii) then, neutralising the resulting mixture with a base or a basic solution.

In stage i), the liquid carboxylic acid is preferably selected from acetic acid, formic acid and propionic acid.

The acidic solution is selected from an aqueous solution of a carboxylic acid or an aqueous solution of a mineral acid. The carboxylic acid for the acidic aqueous solution is selected from acetic acid, formic acid, tartaric acid, oxalic acid, propionic acid or any other carboxylic acid soluble in water. And the mineral acid for the acidic aqueous solution is selected from hydrochloric acid, sulphuric acid or phosphoric acid, among others.

And in stage ii), the base is selected from a basic hydroxide, preferably from sodium hydroxide or potassium hydroxide, or an organic base such as an amine. The basic solution is selected from ammonia, an organic base such as an amine, or a solution of an hydroxide, in which said hydroxide is preferably selected from sodium hydroxide or potassium hydroxide.

A fifth alternative method for obtaining the Granisetron base Form I is characterised in that the following stages are carried out:

i) melting the Granisetron base, and ii) leaving it to cool to give Granisetron base Form I.

Once the Granisetron base Form I has been melted, it can be cooled slowly or rapidly.

The X-ray powder diffractogram of a melted and rapidly cooled sample shows the presence of the Granisetron base Form I together with amorphous Granisetron base.

Figure 5:
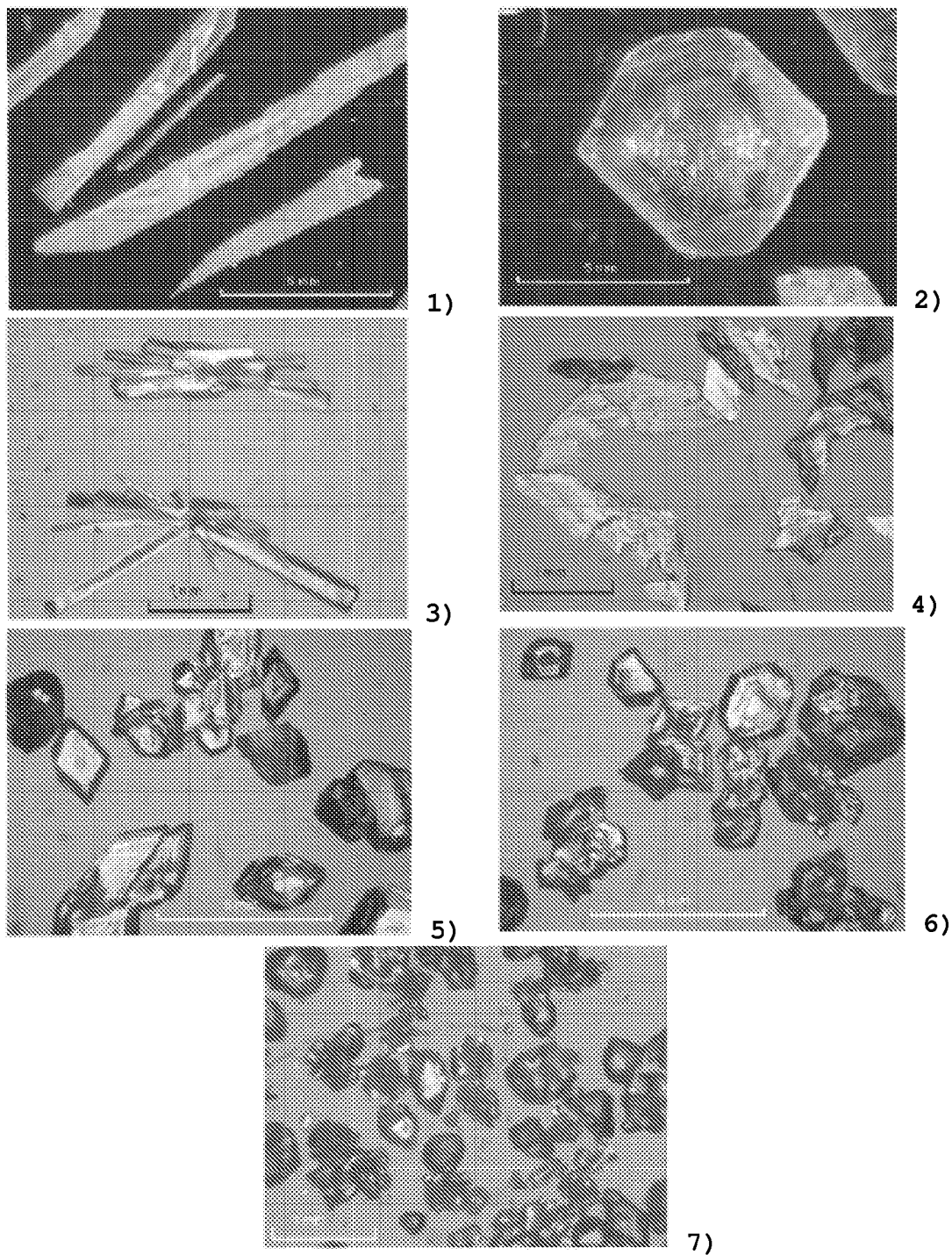
FIG. 5 shows microscopic photographs taken with binocular lens of the crystals of Granisetron base Form I obtained according to various methods defined in accordance with the second object of the invention with different solvents.

The crystalline habit of the crystals obtained thus varies in function of the solvent and the technique used. See FIG. 5 for some examples of crystals obtained according to the different solvents.

A third object of the present invention is to provide a pharmaceutical formulation including Granisetron base Form I together with pharmaceutically acceptable excipients and/or vehicles.

A fourth object of the present invention is to provide a method for preparing the hydrochloride of Granisetron from the Granisetron base Form I, which comprises:

i) dissolving Granisetron base Form I, according to the first object of the invention, in a suitable organic solvent,
ii) adding hydrochloric acid,
iii) evaporating to dryness, and
iv) adding ethyl acetate to precipitate the hydrochloride.

Utilisation of the solid Granisetron base Form I for preparing the Granisetron hydrochloride permits, thanks to the high purity of Granisetron base Form I, the obtaining of Granisetron hydrochloride of acceptable quality for pharmaceutical formulation.

There follow below some examples that set out, by way of non-restrictive illustration of the invention, some preferred embodiments thereof.

EXAMPLES

Example 1

0.5 g of Granisetron base is dissolved in 5 mL of tetrahydrofuran and is left to evaporate at atmospheric pressure and room temperature. This provides 0.5 g of Granisetron base Form I.

Example 2

100 mg of Granisetron base is dissolved in 3 mL of a water/ethanol mixture (4:1) and is left to evaporate at atmospheric pressure and room temperature. This provides 100 mg of Granisetron base Form I.

Example 3

0.5 g of Granisetron base is dissolved in 15 mL of toluene and is evaporated at reduced pressure in a bath at 35-40° C. This provides 0.5 g of Granisetron base Form I.

Example 4

2.0 g of Granisetron base is dissolved in 60 mL of acetone. This solution is poured onto 800 mL of water. The resulting solid is filtered and dried. This provides 1.8 g of Granisetron base Form I.

Example 5

100 mg of Granisetron base is dissolved in 10 mL of a solution of 1N acetic acid. This solution is poured onto 10 mL of a solution of 1N NaOH. It precipitates to a solid that is filtered and dried. This provides 90 mg of Granisetron base Form I.

Example 6

100 mg of Granisetron base is dissolved in 1.0 mL of an 85% formic acid. This solution is poured onto 25 mL of a 20% solution of ammonia. It precipitates to a solid that is filtered and dried. This provides 85 mg of Granisetron base Form I.

Example 7

1.0 g of Granisetron base is mixed with 71 mL of diethyl ether, and is taken to reflux. When all the product has dissolved, the resulting solution is left to cool slowly to room temperature, and crystallises to a solid that is filtered and dried. This provides 0.7 g of Granisetron base Form I.

Example 8

2.23 g of Granisetron base is mixed with 6.0 mL of water and 4.8 mL of 2-propanol, and is taken to reflux, when all dissolves. The resulting solution is left to cool slowly to room temperature, and crystallises to a solid that is filtered and dried. This provides 2.05 g of Granisetron base Form I.

Example 9

130 mg of Granisetron base is dissolved in 1.2 mL of dioxane at 40° C. The solution is cooled to 10° C., and crystallises to a solid that is filtered and dried. This provides 105 mg of Granisetron base Form I.

Example 10

320 mg of Granisetron base is melted in a Pyrex tube heated in a silicone bath and kept at 166° C. for five minutes. It is then left to reach room temperature slowly inside a silicone bath. 320 mg of Granisetron base Form I is recovered.

Example 11

2.61 g of Granisetron base is dissolved in 7.0 ml of 2-propanol, and is taken to reflux, when all the product is dissolved, the resultant dissolution is allowed to cool to 15° C. and the resultant solid is filtered and washed with 2-propanol. 2.47 g of Granisetron base is recovered (95%). Said Granisetron base is characterized as Form I with the following data of XRPD, IR and DSC:

XRPD (° 2θ): 9.8°, 15.4°, 16.2°, 17.4°, 18.3°, 19.0°, 20.8°, 21.2°, 21.7°, 23.5°, 25.4°, 27.1°, 27.7°, 28.1°, 28.7°, 29.0° and 29.3, as shown in FIG. 1.

IR ($cm^{-1}$): 3420, 2920, 2860, 1670, 1530, 1495, 1285, 1210, 770 y 470, as shown in FIG. 2.

DSC: 153±1° C., as shown in FIG. 6.

This characterization was repeated one year later and the same result was obtained, which demonstrates that polymorphic Form I of Granisetron base is stable.

Example 12

A tablet of Granisetron base was formulated with the following composition:

| | | |
|---|---|---|
| GRANISETRON Form I | 10.0 mg | 6.25% |
| ANHYDROUS LACTOSE | 78.9 mg | 49.31% |
| CORN STARCH | 11.2 mg | 7.00% |
| PREGELATINISED STARCH | 11.2 mg | 7.00% |

| | | |
|---|---|---|
| HYPROMELLOSE | 5.1 mg | 3.19% |
| MICROCRYSTALLINE CELLULOSE | 32.0 mg | 20.00% |
| SODIUM CROSCARMELLOSE | 6.0 mg | 3.75% |
| MAGNESIUM STEARATE | 1.6 mg | 1.00% |
| OPADRY WHITE (BASED ON HYPROMELLOSE) | 4.0 mg | 2.50% |

Example 13

1.67 g of Granisetron base Form I is dissolved in 20 mL of isopropanol and 1.1 equivalents of hydrochloric acid are added. The isopropyl alcohol is evaporated practically to dryness and 20 mL of ethyl acetate is added. The precipitate is filtered and dried. This provides 1.44 g (77%) of Granisetron hydrochloride.

What is claimed is:

1. A form of Granisetron base (Form I) having the following positions (°2θ): 9.8°, 15.4°, 16.2°, 17.4°, 18.3°, 19.0°, 20.8°, 21.2°, 21.7°, 23.5°, 25.4°, 27.1°, 27.7°, 28.1°, 28.7°, 29.0° and 29.3° on an X-ray powder diffractogram.

2. The Granisetron base according to claim 1 having absorptions in an IR spectrum recorded on a KBr tablet in the following wavelengths (cm$^{-1}$): 3420, 2920, 2860, 1670, 1530, 1495, 1285, 1210, 770 and 470.

3. A method for obtaining Granisetron base Form I comprising:
dissolving Granisetron base in a suitable polar or apolar organic solvent, or in a mixture thereof, or in a mixture of water-miscible organic solvents and water, at room temperature; and
evaporating the solvent or the mixture of solvents.

4. The method according to claim 3, in which the solvent or mixture of solvents is evaporated at atmospheric pressure.

5. The method according to claim 3, in which the solvent or mixture of solvents is evaporated at reduced pressure.

6. A method for obtaining Granisetron base Form I comprising:
dissolving Granisetron base in a suitable polar or apolar organic solvent or a mixture thereof, or in a mixture of water-miscible organic solvents and water, at a temperature between 30° C. and the reflux temperature of the selected solvent;
leaving the solution to cool to a temperature between 0° C. and room temperature to induce crystallization of the solid; and
filtering the solid.

7. The method according to claim 3, in which the polar or apolar organic solvent is selected from the group consisting of:
methanol, ethanol, 2-propanol, acetone, methyl ethyl ketone, ethyl acetate, acetonitrile, diethyl ether, isopropyl ether, tetrahydrofuran, dioxane, methylene chloride, chloroform, carbon tetrachloride, toluene, and hexane.

8. The method according to claim 6, in which the polar or apolar organic solvent is selected from the group consisting of:
methanol, ethanol, 2-propanol, acetone, methyl ethyl ketone, ethyl acetate, acetonitrile, diethyl ether, isopropyl ether, tetrahydrofuran, dioxane, methylene chloride, chloroform, carbon tetrachloride, toluene, and hexane.

9. The method according to claim 3, in which the water-miscible organic solvent is selected from the group consisting of:
methanol, ethanol, 2-propanol, and acetone.

10. The method according to claim 6, in which the water-miscible organic solvent is selected from the group consisting of:
methanol, ethanol, 2-propanol, and acetone.

11. A method for obtaining Granisetron base Form I comprising:
dissolving Granisetron base in a water-miscible or partially water-miscible organic solvent; and
pouring the solution onto water to precipitate the Granisetron base Form I.

12. The method according to claim 11, wherein the water-miscible or partially water-miscible organic solvent is selected from the group consisting of:
methanol, ethanol, 2-propanol, acetone, and acetonitrile.

13. A method for obtaining Granisetron base Form I comprising:
dissolving Granisetron base in a liquid carboxylic acid, in an acidic solution of carboxylic acid, or in an acidic solution of mineral acid; and
neutralizing the resulting mixture with a base or a basic solution.

14. The method according to claim 13, wherein the liquid carboxylic acid is selected from the group consisting of:
acetic acid, formic acid, and propionic acid.

15. The method according to claim 13, wherein the acidic solution of carboxylic acid is selected from the group consisting of:
acetic acid, formic acid, tartaric acid, oxalic acid, and propionic acid.

16. The method according to claim 13, wherein the acidic solution of mineral acid is selected from the group consisting of:
hydrochloric acid, phosphoric acid, and sulphuric acid.

17. The method according to claim 13, wherein the base is a hydroxide or an organic base.

18. The method according to claim 17, wherein the hydroxide is sodium hydroxide or potassium hydroxide.

19. The method according to claim 17, wherein the organic base is an amine.

20. The method according to claim 13, wherein the basic solution is selected from the group consisting of:
ammonia, an organic base, and a hydroxide solution.

21. The method according to claim 20, wherein the organic base is an amine.

22. The method according to claim 20, wherein the hydroxide is sodium hydroxide or potassium hydroxide.

23. A method for obtaining Granisetron hydrochloride comprising:
dissolving Granisetron base Form I in a suitable organic solvent;
adding hydrochloric acid;
evaporating to dryness; and
adding ethyl acetate to precipitate the hydrochloride.

24. A pharmaceutical formulation comprising Granisetron base Form I and at least one pharmaceutically acceptable excipient or vehicle.

* * * * *